US00PP19998P2

(12) United States Plant Patent
Pieters

(10) Patent No.: US PP19,998 P2
(45) Date of Patent: May 19, 2009

(54) *CHRYSANTHEMUM* PLANT NAMED 'PPP SOR06'

(50) Latin Name: *Chrysanthemum morifolium*
Varietal Denomination: PPP SOR06

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 32 days.

(21) Appl. No.: 11/823,268

(22) Filed: Jun. 27, 2007

(51) Int. Cl.
*A01H 5/00* (2006.01)

(52) U.S. Cl. ..... Plt./290
(58) Field of Classification Search ..... Plt./290
See application file for complete search history.

(56) References Cited

U.S. PATENT DOCUMENTS

PP13,796 P3 * 5/2003 Pieters ..... Plt./290
PP14,473 P3 * 1/2004 Pieters ..... Plt./298

* cited by examiner

*Primary Examiner*—Wendy C. Haas
(74) *Attorney, Agent, or Firm*—Mark P. Bourgeois

(57) ABSTRACT

A new and distinct *Chrysanthemum* plant cultivar is disclosed, characterized by large decorative type inflorescences, consistent flowering response to short days, blooming consistently after 49 days of short day length, pale orange inflorescences with a darker orange center, free branching habit, and a consistent natural season flowering habit during the last week of September.

1 Drawing Sheet

Latin name of the genus and species: *Chrysanthemum morifolium.*
Variety denomination: 'PPP SOR06'.

BACKGROUND OF THE INVENTION

The new cultivar 'PPP SOR06' is a product of a cross between the male parent 'Olawa' (not patented in the United States) and the female parent 'GEDI TWO ARE' (U.S. Plant Pat. No. 14,473). The resulting seeds from the crossing were collected and grown in a greenhouse. The new cultivar was discovered and selected as a single plant by Dirk Pieters in September of 2002 in a cultivated area of Oostnieuwkerke, Belgium.

Asexual reproduction of the new cultivar 'PPP SOR06' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP SOR06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP SOR06.' These characteristics in combination distinguish 'PPP SOR06' as a new and distinct *Chrysanthemum* cultivar:

1. Large, bronze, decorative-type inflorescence;
2. Consistent natural season flowering habit during the last week of September;
3. Free branching habit; and
4. Consistent flowering response to short days, blooming consistently after 49 days of short day length.

Plants of the new cultivar 'PPP SOR06' are similar to plants of the female parent variety, 'GEDI TWO ARE' in most horticultural characteristics, however plants of the new cultivar 'PPP SOR06' has a wider plant spread. Also, the new cultivar 'PPP SOR06' has a smaller inflorescence diameter and more ray florets per inflorescence. Additionally, the ray florets of 'PPP SOR06' are yellow-orange compared to the dark red ray florets of the female patent. Further, the new cultivar has longer inflorescence longevity. Finally, 'PPP SOR06' blooms one to two weeks later than the female parent 'GEDI TWO ARE'.

Plants of the new cultivar 'PPP SOR06' are similar to plants of the male parent variety, 'Olawa' in most horticultural characteristics; however plants of the new cultivar 'PPP SOR06' are taller and wider. Also, the new cultivar 'PPP SOR06' has a smaller inflorescence diameter. Additionally, 'PPP SOR06' has more disc florets per inflorescence. Finally, 'PPP SOR06' has more yellow-orange ray florets compared to the greyed-red ray florets of the male parent.

In comparison to the commercially available variety 'GEDI ONE NOV' (U.S. Plant Pat. No. 13,796), 'PPP SOR06' is shorter but has a wider plant spread. Additionally, the new variety 'PPP SOR06' blooms one to two weeks later than 'GEDI ONE NOV'. Further, the new variety 'PPP SOR06' has a smaller inflorescence diameter and longer inflorescence longevity. Finally, the inflorescences of 'GEDI ONE NOV' are orange with a dark red center whereas the inflorescences of 'PPP SOR06' are yellow-orange with a dark orange center.

BRIEF DESCRIPTION OF THE PHOTOGRAPH

The accompanying drawing illustrates in full color a typical plant of 'PPP SOR06' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP SOR06' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP SOR06.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 21 cm.
Plant spread: Approximately 35 cm.
Growth rate: Moderate.
Branching characteristics: Free Branching.
Length of lateral branches: Approximately 14 cm.
Number of leaves per lateral branch: Approximately 28.
Age of plant described: Approximately 145 days.

FOLIAGE

Leaf:
- *Arrangement.*—Alternate single.
- *Average length.*—Approximately 3.6 cm.
- *Average width.*—Approximately 2.4 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Leaf internode length.*—Approximately 1 cm.
- *Color.*—Young foliage upper side: Near Green 137A. Young foliage under side: Near Green 138A. Mature foliage upper side: Near Green 137A. Mature foliage under side: Near Green 137D.
- *Venation.*—Type: Palmately net. Venation color upper side: Near Green 138C. Venation color under side: Near Green 138C.

Petiole:
- *Average length.*—Approximately 0.5 cm.
- *Color.*—Near Green 138C.
- *Diameter.*—Approximately 0.2 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the last week in September.
- *Number of inflorescences per lateral branch.*—Approximately 11.
- *Inflorescence diameter.*—Approximately 4.2 cm.
- *Inflorescence depth.*—Approximately 1.5 cm.
- *Inflorescence longevity on plant.*—Approximately 28 to 34 days.
- *Persistence.*—Persistent.

Ray florets:
- *Appearance.*—Matte.
- *Texture.*—Smooth.
- *Average number of ray florets per inflorescence.*—180.
- *Shape.*—Oblanceolate.
- *Aspect.*—Flat.
- *Margin.*—Entire.
- *Apex.*—Obtuse.
- *Length.*—Approximately 1.5 cm.
- *Width.*—Approximately 0.3 cm.
- *Color.*—Upper surface at first opening: Near Greyed-Red 180A with longitudinal lines of near Yellow 7A concentrated at the base. Upper surface at maturity: Near Yellow-Orange 20A with longitudinal lines of near Yellow 7A concentrated at the base. Upper surface at fading: Near Yellow 7C with faint longitudinal lines of near Greyed-Red 179A. Under surface at first opening: Near Greyed-Red 180A with faint longitudinal lines of near Yellow 7B concentrated at the base. Under surface at maturity: Near Greyed-Red 181A with faint longitudinal lines of near Yellow 7B concentrated at the base. Under surface at fading: Near Yellow 8B with faint longitudinal lines of near Greyed-Red 179B. Center ray florets: Near Greyed-Orange 171A.

Disc florets:
- *Appearance.*—Shiny.
- *Texture.*—Smooth.
- *Average number of florets per disc.*—Approximately 19.
- *Shape.*—Cylindric.
- *Apex.*—Obtuse.
- *Average length.*—Approximately 0.3 cm.
- *Average width.*—Approximately 0.1 cm.
- *Color.*—At first opening: Near Yellow 9A. At maturity: Near Yellow 9A. At fading: Near Yellow 9A.

Peduncle:
- *Length.*—At terminal end (shortest): Approximately 4 cm. At lateral end (longest): Approximately 6.8 cm.
- *Angle to stem.*—Acute.
- *Strength.*—Moderate.
- *Color.*—Near Green 138A.
- *Habit.*—Upright.
- *Diameter.*—Approximately 0.2 cm.
- *Surface texture.*—Lightly pubescent.

Inflorescence bud:
- *Length.*—Approximately 1 cm.
- *Diameter.*—Approximately 0.8 cm.
- *Form.*—Globular.
- *Color.*—Near Greyed-Red 179A.

Involucral bracts (phyllaries):
- *Appearance.*—Matte.
- *Texture.*—Lightly pubescent.
- *Number.*—Approximately 20.
- *Shape.*—Ovate.
- *Margin.*—Entire.
- *Apex.*—Acute.
- *Length.*—Approximately 1 cm.
- *Width.*—Approximately 0.3 cm.

*Color.*—Upper side: Near Green 138A. Under side: Near Green 138B.

REPRODUCTIVE ORGANS

Ray florets:
*Number of pistils per floret.*—1.
*Stigma shape.*—2 branched.
*Stigma color.*—Near Yellow 7A.
*Style color.*—Near Green-Yellow 1C.
*Style length.*—Approximately 0.2 cm.
*Stamens.*—Absent.

Disc florets:
*Number of pistils per floret.*—1.
*Stigma shape.*—Cylindric.
*Stigma color.*—Near Yellow 9A.
*Style length.*—Approximately 0.1 cm.
*Style color.*—Near Green-Yellow 1D.
*Number of stamens per floret.*—Approximately 5.
*Anther shape.*—Tubular.
*Anther color.*—Near Yellow 9A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new distinct cultivar of *Chrysanthemum* plant named 'PPP SOR06' as herein illustrated and described.

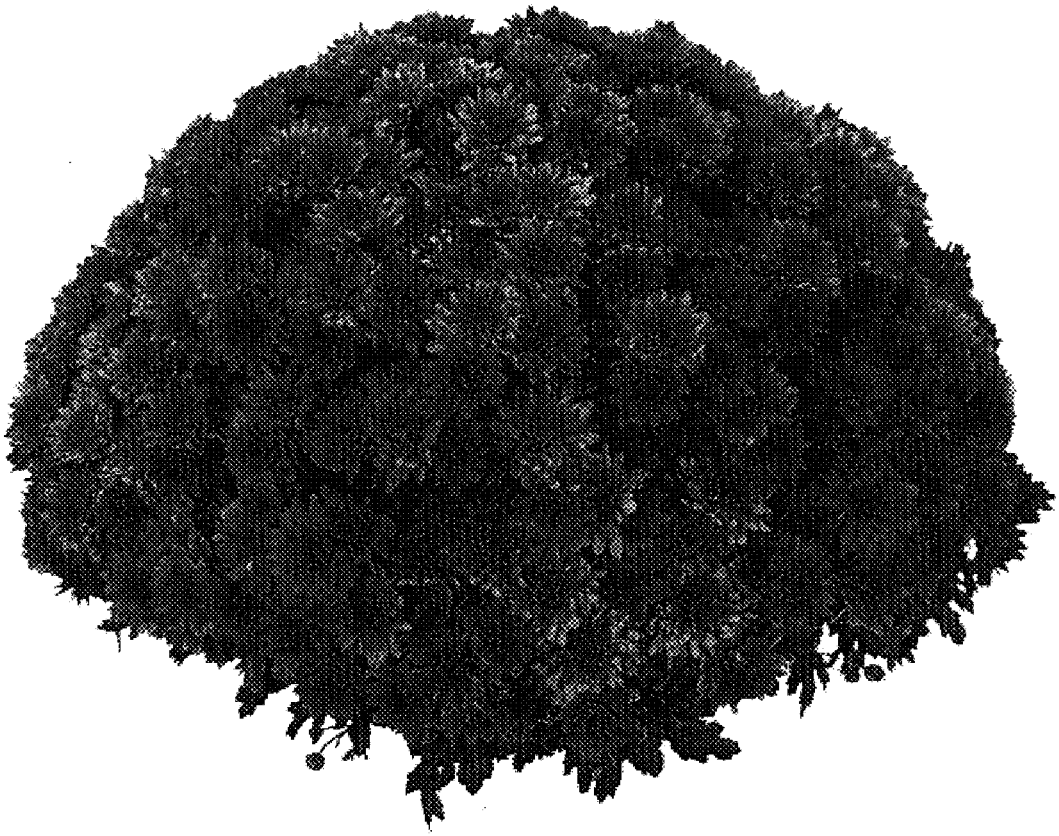

* * * * *